United States Patent [19]

Kotewicz et al.

[11] Patent Number: 5,405,776
[45] Date of Patent: Apr. 11, 1995

[54] CLONED GENES ENCODING REVERSE TRANSCRIPTASE LACKING RNASE H ACTIVITY

[75] Inventors: Michael L. Kotewicz, Columbia; Gary F. Gerard, Frederick, both of Md.

[73] Assignee: Life Technologies, Inc., Gaithersburg, Md.

[21] Appl. No.: 825,260

[22] Filed: Jan. 24, 1992

Related U.S. Application Data

[60] Division of Ser. No. 671,156, Mar. 18, 1991, which is a continuation of Ser. No. 143,396, Jan. 13, 1988, abandoned.

[51] Int. Cl.$^6$ ............... C12N 9/12; C12N 15/00; C12N 15/54; C12N 15/70
[52] U.S. Cl. ............... 435/252.33; 536/23.4; 536/23.2; 435/194; 435/69.1; 435/69.7; 435/252.3; 435/320.1; 935/10; 935/14; 935/29; 935/36; 935/47; 935/66; 935/73
[58] Field of Search ............... 435/69.1, 69.7, 172.3, 435/193, 194, 252.3, 252.33, 320.1; 536/23.2, 23.4

[56] References Cited

U.S. PATENT DOCUMENTS

| | | | |
|---|---|---|---|
| 4,663,290 | 5/1987 | Weis et al. | 435/253 |
| 4,943,531 | 7/1990 | Groff et al. | 435/194 |
| 5,017,492 | 5/1991 | Kotewicz et al. | 435/252.3 |

OTHER PUBLICATIONS

Gerard, G. F., et al., 1974, Biochemistry, 13:1632–1641.
Gerard, G. F., et al., 1975, Journal of Virology, 15:785–797.
Lai, M. H. T., et al., 1978, Journal of Virology, 25:652–663.
Gerard, G. F., et al., 1978, Journal of Virology, 26:16–28.
Gerwin, B. I., et al., 1974, Journal of Virology, 31:741–751.
Moelling, K., et al., 1979, Journal of Virology, 32:370–378.
Tronick, S. R., et al., 1974, Proceedings of the National Academy of Sciences, U.S.A., 76:6314–6318.
Bussin, R. H., et al., 1980, Journal of Virology, 35(2):287–297.
Gerard, G. F., et al., 1981, Journal of Virology, 37:748–754.
Shinnick, T. M., et al., 1981, Nature, 293:543–548.
Maniatis, T., et al., 1982, in *Molecular Cloning: A Laboratory Manual*, Cold Spring Harbor Laboratory Press, pp. 213 and 231.
Toh, H., et al., 1983, Nature, 305:827–829.
Kamer, G., et al., 1984, *Nucleic Acids Research*, 12(18):7269–7282.
Smith, J. K., et al., 1984, Journal of Virology, 49(1):200–204.
Finston, W. I., et al., 1984, Journal of Virology, 51(1):26–33.
Levin, J. G., et al., 1984, Journal of Virology, 51(2):470–478.
Resnick, R., et al., 1984, Journal of Virology, 51(3):813–821.

(List continued on next page.)

*Primary Examiner*—Robert A. Wax
*Assistant Examiner*—William W. Moore
*Attorney, Agent, or Firm*—Sterne, Kessler, Goldstein & Fox

[57] ABSTRACT

The invention relates to a gene which encodes reverse transcriptase having DNA polymerase activity and substantially no RNase H activity. The invention also relates to vectors containing the gene and hosts transformed with the vectors of the invention. The invention also relates to a method of producing reverse transcriptase having DNA polymerase activity and substantially no RNase H activity by expressing the reverse transcriptase genes of the present invention in a host. The invention also relates to a method of producing cDNA from mRNA using the reverse transcriptase of the invention. The invention also relates to a kit for the preparation of cDNA from mRNA comprising the reverse transcriptase of the invention.

9 Claims, 8 Drawing Sheets

OTHER PUBLICATIONS

Kotewicz, M. L., et al., 1985, Gene 35:249-258.
Tanese, N., et al., 1985, Proceedings of the National Academy of Sciences, U.S.A., 82:4944-4948.
Roth, M. J., et al., 1985, Journal of Biological Chemistry, 260:9326-9335.
Tanese, N., et al., 1986, Journal of Virology 59(2):328-340.
Kotewicz, M. L., et al., 1988, Nucleic Acids Research, 16:265-277.
Lai, M. H. T., et al., 1978, Journal of Virology, 27:823-825.
Van Beveren, L., et al., 1985, in RNA Tumor Viruses, 2nd Edition, vol. 2, Cold Spring Harbor Laboratory Press, pp. 773-779.
Michel, F., et al., 1985, Nature 316:641-643.
Fawcett, D. H., et al., 1986, Cell 47:1007-1015.
Akins, R. A., et al., 1986, Cell 47:505-516.
Gerard, G. F., et al., 1986, DNA, 5:271-279.
Johnson, M. S., et al., 1986, Proceedings of the National Academy of Sciences, U.S.A. 83:7648-7652.
Messer, L. I. et al., Virology 146:146(1985).

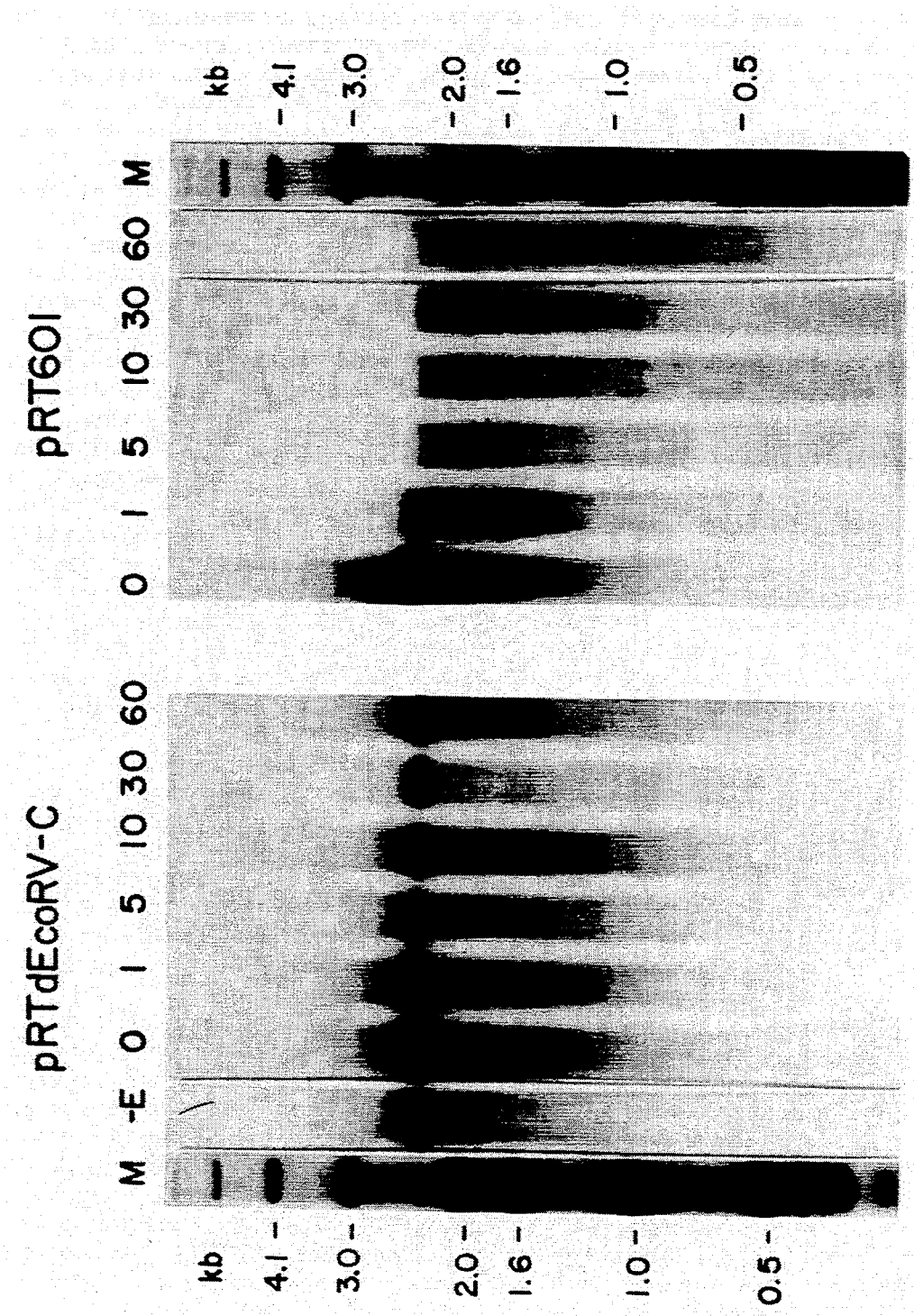

```
                                            .              .             .            1078
ATG ACC CTA AAT ATA GAA GAT GAG CAT CGG CTA CAT GAG ACC TCA AAA GAG CCA GAT GTT
MET Thr Leu Asn Ile Glu Asp Glu His Arg Leu His Glu Thr Ser Lys Glu Pro Asp Val

1138
TCT CTA GGG TCC ACA TGG CTG TCT GAT TTT CCT CAG GCC TGG GCG GAA ACC GGG GGC ATG
Ser Leu Gly Ser Thr Trp Leu Ser Asp Phe Pro Gln Ala Trp Ala Glu Thr Gly Gly MET

1198
GGA CTG GCA GTT CGC CAA GCT CCT CTG ATC ATA CCT CTG AAA GCA ACC TCT ACC CCC GTG
Gly Leu Ala Val Arg Gln Ala Pro Leu Ile Ile Pro Leu Lys Ala Thr Ser Thr Pro Val

1258
TCC ATA AAA CAA TAC CCC ATG TCA CAA GAA GCC AGA CTG GGG ATC AAG CCC CAC ATA CAG
Ser Ile Lys Gln Tyr Pro MET Ser Gln Glu Ala Arg Leu Gly Ile Lys Pro His Ile Gln

1318
AGA CTG TTG GAC CAG GGA ATA CTG GTA CCC TGC CAG TCC CCC TGG AAC ACG CCC CTG CTA
Arg Leu Leu Asp Gln Gly Ile Leu Val Pro Cys Gln Ser Pro Trp Asn Thr Pro Leu Leu

1378
CCC GTT AAG AAA CCA GGG ACT AAT GAT TAT AGG CCT GTC CAG GAT CTG AGA GAA GTC AAC
Pro Val Lys Lys Pro Gly Thr Asn Asp Tyr Arg Pro Val Gln Asp Leu Arg Glu Val Asn

1438
AAG CGG GTG GAA GAC ATC CAC CCC ACC GTG CCC AAC CCT TAC AAC CTC TTG AGC GGG CTC
Lys Arg Val Glu Asp Ile His Pro Thr Val Pro Asn Pro Tyr Asn Leu Leu Ser Gly Leu

1438
AAG CGG GTG GAA GAC ATC CAC CCC ACC GTG CCC AAC CCT TAC AAC CTC TTG AGC GGG CTC
Lys Arg Val Glu Asp Ile His Pro Thr Val Pro Asn Pro Tyr Asn Leu Leu Ser Gly Leu

1498
CCA CCG TCC CAC CAG TGG TAC ACT GTG CTT GAT TTA AAG GAT GCC TTT TTC TGC CTG AGA
Pro Pro Ser His Gln Trp Tyr Thr Val Leu Asp Leu Lys Asp Ala Phe Phe Cys Leu Arg
```

FIG.6A

```
                                                                    1558
CTC CAC CCC ACC AGT CAG CCT CTC TTC GCC TTT GAG TGG AGA GAT CCA GAG ATG GGA ATC
Leu His Pro Thr Ser Gln Pro Leu Phe Ala Phe Glu Trp Arg Asp Pro Glu MET Gly Ile

1618
TCA GGA CAA TTG ACC TGG ACC AGA CTC CCA CAG GGT TTC AAA AAC AGT CCC ACC CTG TTT
Ser Gly Gln Leu Thr Trp Thr Arg Leu Pro Gln Gly Phe Lys Asn Ser Pro Thr Leu Phe

1678
GAT GAG GCA CTG CAC AGA GAC CTA GCA GAC TTC CGG ATC CAG CAC CCA GAC TTG ATC CTG
Asp Glu Ala Leu His Arg Asp Leu Ala Asp Phe Arg Ile Gln His Pro Asp Leu Ile Leu

1738
CTA CAG TAC GTG GAT GAC TTA CTG CTG GCC GCC ACT TCT GAG CTA GAC TGC CAA CAA GGT
Leu Gln Tyr Val Asp Asp Leu Leu Leu Ala Ala Thr Ser Glu Leu Asp Cys Gln Gln Gly

1798
ACT CGG GCC CTG TTA CAA ACC CTA GGG AAC CTC GGG TAT CGG GCC TCG GCC AAG AAA GCC
Thr Arg Ala Leu Leu Gln Thr Leu Gly Asn Leu Gly Tyr Arg Ala Ser Ala Lys Lys Ala

1858
CAA ATT TGC CAG AAA CAG GTC AAG TAT CTG GGG TAT CTT CTA AAA GAG GGT CAG AGA TGG
Gln Ile Cys Gln Lys Gln Val Lys Tyr Leu Gly Tyr Leu Leu Lys Glu Gly Gln Arg Trp

1918
CTG ACT GAG GCC AGA AAA GAG ACT GTG ATG GGG CAG CCT ACT CCG AAG ACC CCT CGA CAA
Leu Thr Glu Ala Arg Lys Glu Thr Val MET Gly Gln Pro Thr Pro Lys Thr Pro Arg Gln

1978
CTA AGG GAG TTC CTA GGG ACG GCA GGC TTC TGT CGC CTC TGG ATC CCT GGG TTT GCA GAA
Leu Arg Glu Phe Leu Gly Thr Ala Gly Phe Cys Arg Leu Trp Ile Pro Gly Phe Ala Glu

2038
ATG GCA GCC CCC TTG TAC CCT CTC ACC AAA ACG GGG ACT CTG TTT AAT TGG GGC CCA GAC
MET Ala Ala Pro Leu Tyr Pro Leu Thr Lys Thr Gly Thr Leu Phe Asn Trp Gly Pro Asp
```

FIG.6B

```
                                                            2098
CAA CAA AAG GCC TAT CAA GAA ATC AAG CAA GCT CTT CTA ACT GCC CCA GCC CTG GGG TTG
Gln Gln Lys Ala Tyr Gln Glu Ile Lys Gln Ala Leu Leu Thr Ala Pro Ala Leu Gly Leu

2158
CCA GAT TTG ACT AAG CCC TTT GAA CTC TTT GTC GAC GAG AAG CAG GGC TAC GCC AAA GGT
Pro Asp Leu Thr Lys Pro Phe Glu Leu Phe Val Asp Glu Lys Gln Gly Tyr Ala Lys Gly

2218
GTC CTA ACG CAA AAA CTG GGA CCT TGG CGT CGG CCG GTG GCC TAC CTG TCC AAA AAG CTA
Val Leu Thr Gln Lys Leu Gly Pro Trp Arg Arg Pro Val Ala Tyr Leu Ser Lys Lys Leu

2278
GAC CCA GTA GCA GCT GGG TGG CCC CCT TGC CTA CGG ATG GTA GCA GCC ATT GCC GTA CTG
Asp Pro Val Ala Ala Gly Trp Pro Pro Cys Leu Arg MET Val Ala Ala Ile Ala Val Leu

2338
ACA AAG GAT GCA GGC AAG CTA ACC ATG GGA CAG CCA CTA GTC ATT CTG GCC CCC CAT GCA
Thr Lys Asp Ala Gly Lys Leu Thr MET Gly Gln Pro Leu Val Ile Leu Ala Pro His Ala

2398
GTA GAG GCA CTA GTC AAA CAA CCC CCC GAC CGC TGG CTT TCC AAC GCC CGG ATG ACT CAC
Val Glu Ala Leu Val Lys Gln Pro Pro Asp Arg Trp Leu Ser Asn Ala Arg MET Thr His

2458
TAT CAG GCC TTG CTT TTG GAC ACG GAC CGG GTC CAG TTC GGA CCG GTG GTA GCC CTG AAC
Tyr Gln Ala Leu Leu Leu Asp Thr Asp Arg Val Gln Phe Gly Pro Val Val Ala Leu Asn

2518
CCG GCT ACG CTG CTC CCA CTG CCT GAG GAA GGG CTG CAA CAC AAC TGC CTT GAT AAT TCC
Pro Ala Thr Leu Leu Pro Leu Pro Glu Glu Gly Leu Gln His Asn Cys Leu Asp Asn Ser

2533
CGC TTA ATT AAT TAA
Arg Leu Ile Asn
```

FIG. 6C

CLONED GENES ENCODING REVERSE TRANSCRIPTASE LACKING RNASE H ACTIVITY

This application is a division of application Ser. No. 07/671,156, filed Mar. 18, 1991, which is a continuation of application Ser. No. 07/143,396, filed Jan. 13, 1988, abandoned.

FIELD OF THE INVENTION

The invention is in the field of recombinant genetics.

BACKGROUND OF THE INVENTION

Both viral and cloned reverse transcriptase (RT) contain at least two enzymatic activities, DNA polymerase and ribonuclease H (RNase H), that reside on a single polypeptide. Grandgenett, D. P. et al., *Proc. Natl. Acad. Sci. (USA)* 70:230-234 (1973); Moelling, K., *Virology* 62:46-59 (1974); Kotewicz, M. L., et al., *Gene* 35:249-258 (1985); and Roth, M. J., et al., *J. Biol. Chem.* 260:9326-9335 (1985). Little is known about the structure-functional relationship of these two activities, but such knowledge would be important both in understanding retroviral replication and in exploiting the enzyme as a recombinant DNA tool.

In the retrovirus life cycle, the RT DNA polymerase activity is responsible for transcribing viral RNA into double-stranded DNA. Varmus, H. (1982), in Weiss, R., et al. (eds.), *RNA Tumor Viruses*, Cold Spring Harbor Laboratory, pp. 410-423. The function of RNase H in replication is less clear, but it is thought to degrade genomic RNA during DNA synthesis to generate oligomeric RNA primers for plus-strand DNA synthesis, and to remove the RNA primers of both minus- and plus-strand DNA. Omer, C. A., et al., *Cell* 30:797-805 (1982); Resnick, R., et al., *J. Virol.* 51:813-821 (1984); Varmus, H. (1985), in Weiss, R., et al. (eds.), *RNA Tumor Viruses*, Cold Spring Harbor Laboratory, pp. 79-80.

The temporal relationship in vivo between DNA polymerization and RNA hydrolysis is not well defined. Furthermore, precisely how the two enzymatic activities are coordinated is not clear. Conditional mutations restricted to either DNA polymerase or RNase H would be invaluable in deciphering the events of retroviral replication. Unfortunately, conditional viral mutations in the RT gene invariably affect both activities. Lai, M. H. T. et al., *J. Virol.* 27:823-825 (1978); Moelling, K., et al., *J. Virol.* 32:370-378 (1979).

RT is used extensively in recombinant DNA technology to synthesize cDNA from mRNA. One major problem with cDNA synthesis is that the RNase H activity of RT degrades the mRNA template during first-strand synthesis. The mRNA poly(A)-oligo(dT) hybrid used as a primer for first-strand cDNA synthesis is degraded by RT RNase H. Thus, at the outset of cDNA synthesis, a competition is established between RNase H-mediated deadenylation of mRNA and initiation of DNA synthesis, which reduces the yield of cDNA product. Berger, S. L., et al., *Biochem.* 22:2365-2373 (1983). Furthermore, in some cases, the RNase H causes premature termination of DNA chain growth. Unfortunately, these events eliminate the potential for repeated copying of the RNA template.

Efforts to selectively inactivate RT RNase H with site-specific inhibitors have been unsuccessful (for review, see Gerard, G. F. (1983), in Jacob, S. T., (ed.), *Enzymes of Nucleic Acid Synthesis and Modification*, Vol. I, DNA Enzymes, CRC Press, Inc., Boca Raton, Fla., pp. 1-38). Attempts to physically separate the active centers of RT polymerase and RNase H activity by proteolysis have yielded a proteolytic fragment possessing only RNase H activity (Lai, M. H. T., et al., *J. virol.* 25:652-663 (1978); Gerard, G. F., *J. Virol.* 26:16-28 (1978); and Gerard, G. F., *J. Virol.* 37:748-754 (1981)), but no corresponding fragment containing only polymerase activity has been isolated.

Computer analysis of the amino acid sequences from the putative gene products of retroviral pol genes has revealed a 150-residue segment at the carboxyl terminus that is homologous with the ribonuclease H of *E. coli* and a section close to the amino terminus which can be aligned with nonretroviral polymerases. Johnson, M. S., et al., *Proc. Natl. Acad. Sci. (USA)* 83:7648-7652 (1986). Based on these related amino acid sequences, Johnson et al. suggest that ribonuclease H activity should be situated at the carboxyl terminus, and the DNA polymerase activity at the amino terminus.

There have been a number of reports concerning the cloning of genes which encode RT and their expression in hosts. Weiss et al., U.S. Pat. No. 4,663,290 (1987); Gerard, G. F., *DNA* 5:271-279 (1986); Kotewicz, M. L., et al., *Gene* 35:249-258 (1985); Tanese, N., et al., *Proc. Natl. Acad. Sci. (USA)* 82:4944-4948 (1985); and Roth, M. J., et al., *J. Biol. Chem.* 260:9326-9335 (1985).

There has been no direct scientific evidence that amino acid residues involved catalytically or structurally in the RNase H activity of reverse transcriptase could be altered to eliminate RNase H activity without affecting the RNA-dependant DNA polymerase activity of reverse transcriptase. Moreover, there has been no report of the cloning of RT to give a gene product without RNase activity.

SUMMARY OF THE INVENTION

The invention relates to a gene which encodes reverse transcriptase having DNA polymerase activity and substantially no RNase H activity.

The invention also relates to a reverse transcriptase gene comprising the following DNA sequence:

```
                                                                          1078
ATG ACC CTA AAT ATA GAA GAT GAG CAT CGG CTA CAT GAG ACC TCA AAA GAG CCA GAT GTT
MET Thr Leu Asn Ile Glu Asp Glu His Arg Leu His Glu Thr Ser Lys Glu Pro Asp Val

1138
TCT CTA GGG TCC ACA TGG CTG TCT GAT TTT CCT CAG GCC TGG GCG GAA ACC GGG GGC ATG
Ser Leu Gly Ser Thr Trp Leu Ser Asp Phe Pro Gln Ala Trp Ala Glu Thr Gly Gly MET

1198
GGA CTG GCA GTT CGC CAA GCT CCT CTG ATC ATA CCT CTG AAA GCA ACC TCT ACC CCC GTG
Gly Leu Ala Val Arg Gln Ala Pro Leu Ile Ile Pro Leu Lys Ala Thr Ser Thr Pro Val
```

-continued

```
                                                                           1258
TCC ATA AAA CAA TAC CCC ATG TCA CAA GAA GCC AGA CTG GGG ATC AAG CCC CAC ATA CAG
Ser Ile Lys Gln Tyr Pro MET ser Gln Glu Ala Arg Leu Gly Ile Lys Pro His Ile Gln 1318
AGA CTG TTG GAC CAG GGA ATA CTG GTA CCC TGC CAG TCC CCC TGG AAC ACG CCC CTG CTA
Arg Leu Leu Asp Gln Gly Ile Leu Val Pro Cys Gln Ser Pro Trp Asn Thr Pro Leu Leu 1378
CCC GTT AAG AAA CCA GGG ACT AAT GAT TAT AGG CCT GTC CAG GAT CTG AGA GAA GTC AAC
Pro Val Lys Lys Pro Gly Thr Asn Asp Tyr Arg Pro Val Gln Asp Leu Arg Glu Val Asn 1438
AAG CGG GTG GAA GAC ATC CAC CCC ACC GTG CCC AAC CCT TAC AAC CTC TTG AGC GGG CTC
Lys Arg Val Glu Asp Ile His Pro Thr Val Pro Asn Pro Tyr Asn Leu Leu Ser Gly Leu 1498
CCA CCG TCC CAC CAG TGG TAC ACT GTG CTT GAT TTA AAG GAT GCC TTT TTC TGC CTG AGA
Pro Pro Ser His Gln Trp Tyr Thr Val Leu Asp Leu Lys Asp Ala Phe Phe Cys Leu Arg 1558
CTC CAC CCC ACC AGT CAG CCT CTC TTC GCC TTT GAG TGG AGA GAT CCA GAG ATG GGA ATC
Leu His Pro Thr Ser Gln Pro Leu Phe Ala Phe Glu Trp Arg Asp Pro Glu MET Gly Ile 1618
TCA GGA CAA TTG ACC TGG ACC AGA CTC CCA CAG GGT TTC AAA AAC AGT CCC ACC CTG TTT
Ser Gly Gln Leu Thr Trp Thr Arg Leu Pro Gln Gly Phe Lys Asn Ser Pro Thr Leu Phe 1678
GAT GAG GCA CTG CAC AGA GAC CTA GCA GAC TTC CGG ATC CAG CAC CCA GAC TTG ATC CTG
Asp Glu Ala Leu His Arg Asp Leu Ala Asp Phe Arg Ile Gln His Pro Asp Leu Ile Leu 1738
CTA CAG TAC GTG GAT GAC TTA CTG CTG GCC GCC ACT TCT GAG CTA GAC TGC CAA CAA GGT
Leu Gln Tyr Val Asp Asp Leu Leu Leu Ala Ala Thr Ser Glu Leu Asp Cys Gln Gln Gly 1798
ACT CGG GCC CTG TTA CAA ACC CTA GGG AAC CTC GGG TAT CGG GCC TCG GCC AAG AAA GCC
Thr Arg Ala Leu Leu Gln Thr Leu Gly Asn Leu Gly Tyr Arg Ala Ser Ala Lys Lys Ala 1858
CAA ATT TGC CAG AAA CAG GTC AAG TAT CTG GGG TAT CTT CTA AAA GAG GGT CAG AGA TGG
Gln Ile Cys Gln Lys Gln Val Lys Tyr Leu Gly Tyr Leu Leu Lys Glu Gly Gln Arg Trp 1918
CTG ACT GAG GCC AGA AAA GAG ACT GTG ATG GGG CAG CCT ACT CCG AAG ACC CCT CGA CAA
Leu Thr Glu Ala Arg Lys Glu Thr Val MET Gly Gln Pro Thr Pro Lys Thr Pro Arg Gln 1978
CTA AGG GAG TTC CTA GGG ACG GCA GGC TTC TGT CGC CTC TGG ATC CCT GGG TTT GCA GAA
Leu Arg Glu Phe Leu Gly Thr Ala Gly Phe Cys Arg Leu Trp Ile Pro Gly Phe Ala Glu 2038
ATG GCA GCC CCC TTG TAC CCT CTC ACC AAA ACG GGG ACT CTG TTT AAT TGG GGC CCA GAC
MET Ala Ala Pro Leu Tyr Pro Leu Thr Lys Thr Gly Thr Leu Phe Asn Trp Gly Pro Asp 2098
CAA CAA AAG GCC TAT CAA GAA ATC AAG CAA GCT CTT CTA ACT GCC CCA GCC CTG GGG TTG
Gln Gln Lys Ala Tyr Gln Glu Ile Lys Gln Ala Leu Leu Thr Ala Pro Ala Leu Gly Leu 2158
CCA GAT TTG ACT AAG CCC TTT GAA CTC TTT GTC GAC GAG AAG CAG GGC TAC GCC AAA GGT
Pro Asp Leu Thr Lys Pro Phe Glu Leu Phe Val Asp Glu Lys Gln Gly Tyr Ala Lys Gly 2218
GTC CTA ACG CAA AAA CTG GGA CCT TGG CGT CGG CCG GTG GCC TAC CTG TCC AAA AAG CTA
Val Leu Thr Gln Lys Leu Gly Pro Trp Arg Arg Pro Val Ala Tyr Leu Ser Lys Lys Leu 2278
GAC CCA GTA GCA GCT GGG TGG CCC CCT TGC CTA CGG ATG GTA GCA GCC ATT GCC GTA CTG
Asp Pro Val Ala Ala Gly Trp Pro Pro Cys Leu Arg MET Val Ala Ala Ile Ala Val Leu 2338
ACA AAG GAT GCA GGC AAG CTA ACC ATG GGA CAG CCA CTA GTC ATT CTG GCC CCC CAT GCA
Thr Lys Asp Ala Gly Lys Leu Thr MET Gly Gln Pro Leu Val Ile Leu Ala Pro His Ala 2398
GTA GAG GCA CTA GTC AAA CAA CCC CCC GAC CGC TGG CTT TCC AAC GCC CGG ATG ACT CAC
Val Glu Ala Leu Val Lys Gln Pro Pro Asp Arg Trp Leu Ser Asn Ala Arg MET Thr His
```

```
                                                                              2458
TAT CAG GCC TTG CTT TTG GAC ACG GAC CGG GTC CAG TTC GGA CCG GTG GTA GCC CTG AAC
Tyr Gln Ala Leu Leu Leu Asp Thr Asp Arg Val Gln Phe Gly Pro Val Val Ala Leu Asn

2512
CCG GCT ACG CTG CTC CCA CTG CCT GAG GAA GGG CTG CAA CAC AAC TGC CTT GAT
Pro Ala Thr Leu Leu Pro Leu Pro Glu Glu Gly Leu Gln His Asn Cys Leu Asp
``` or the degenerate variants thereof.

The invention also relates to a reverse transcriptase 10 gene comprising the following DNA sequence:

```
                                                                              1078
ATG ACC CTA AAT ATA GAA GAT GAG CAT CGG CTA CAT GAG ACC TCA AAA GAG CCA GAT GTT
MET Thr Leu Asn Ile Glu Asp Glu His Arg Leu His Glu Thr Ser Lys Glu Pro Asp Val

1138
TCT CTA GGG TCC ACA TGG CTG TCT GAT TTT CCT CAG GCC TGG GCG AAA ACC GGG GGC ATG
Ser Leu Gly Ser Thr Trp Leu Ser Asp Phe Pro Gln Ala Trp Ala Glu Thr Gly Gly MET

1198
GGA CTG GCA GTT CGC CAA GCT CCT CTG ATC ATA CCT CTG AAA GCA ACC TCT ACC CCC GTG
Gly Leu Ala Val Arg Gln Ala Pro Leu Ile Ile Pro Leu Lys Ala Thr Ser Thr Pro Val

1258
TCC ATA AAA CAA TAC CCC ATG TCA CAA GAA GCC AGA CTG GGG ATC AAG CCC CAC ATA CAG
Ser Ile Lys Gln Tyr Pro MET ser Gln Glu Ala Arg Leu Gly Ile Lys Pro His Ile Gln 1318
AGA CTG TTG GAC CAG GGA ATA CTG GTA CCC TGC CAG TCC CCC TGG AAC ACG CCC CTG CTA
Arg Leu Leu Asp Gln Gly Ile Leu Val Pro Cys Gln Ser Pro Trp Asn Thr Pro Leu Leu 1378
CCC GTT AAG AAA CCA GGG ACT AAT GAT TAT AGG CCT GTC CAG GAT CTG AGA GAA GTC AAC
Pro Val Lys Lys Pro Gly Thr Asn Asp Tyr Arg Pro Val Gln Asp Leu Arg Glu Val Asn 1438
AAG CGG GTG GAA GAC ATC CAC CCC ACC GTG CCC AAC CCT TAC AAC CTC TTG AGC GGG CTC
Lys Arg Val Glu Asp Ile His Pro Thr Val Pro Asn Pro Tyr Asn Leu Leu Ser Gly Leu 1498
CCA CCG TCC CAC CAG TGG TAC ACT GTG CTT GAT TTA AAG GAT GCC TTT TTC TGC CTG AGA
Pro Pro Ser His Gln Trp Tyr Thr Val Leu Asp Leu Lys Asp Ala Phe Phe Cys Leu Arg 1558
CTC CAC CCC ACC AGT CAG CCT CTC TTC GCC TTT GAG TGG AGA GAT CCA GAG ATG GGA ATC
Leu His Pro Thr Ser Gln Pro Leu Phe Ala Phe Glu Trp Arg Asp Pro Glu MET Gly Ile 1618
TCA GGA CAA TTG ACC TGG ACC AGA CTC CCA CAG GGT TTC AAA AAC AGT CCC ACC CTG TTT
Ser Gly Gln Leu Thr Trp Thr Arg Leu Pro Gln Gly Phe Lys Asn Ser Pro Thr Leu Phe 1678
GAT GAG GCA CTG CAC AGA GAC CTA GCA GAC TTC CGG ATC CAG CAC CCA GAC TTG ATC CTG
Asp Glu Ala Leu His Arg Asp Leu Ala Asp Phe Arg Ile Gln His Pro Asp Leu Ile Leu 1738
CTA CAG TAC GTG GAT GAC TTA CTG CTG GCC GCC ACT TCT GAG CTA GAC TGC CAA CAA GGT
Leu Gln Tyr Val Asp Asp Leu Leu Leu Ala Ala Thr Ser Glu Leu Asp Cys Gln Gln Gly 1798
ACT CGG GCC CTG TTA CAA ACC CTA GGG AAC CTC GGG TAT CGG GCC TCG GCC AAG AAA GCC
Thr Arg Ala Leu Leu Gln Thr Leu Gly Asn Leu Gly Tyr Arg Ala Ser Ala Lys Lys Ala 1858
CAA ATT TGC CAG AAA CAG GTC AAG TAT CTG GGG TAT CTT CTA AAA GAG GGT CAG AGA TGG
Gln Ile Cys Gln Lys Gln Val Lys Tyr Leu Gly Tyr Leu Leu Lys Glu Gly Gln Arg Trp 1918
CTG ACT GAG GCC AGA AAA GAG ACT GTG ATG GGG CAG CCT ACT CCG AAG ACC CCT CGA CAA
Leu Thr Glu Ala Arg Lys Glu Thr Val MET Gly Gln Pro Thr Pro Lys Thr Pro Arg Gln 1978
CTA AGG GAG TTC CTA GGG ACG GCA GGC TTC TGT CGC CTC TGG ATC CCT GGG TTT GCA GAA
Leu Arg Glu Phe Leu Gly Thr Ala Gly Phe Cys Arg Leu Trp Ile Pro Gly Phe Ala Glu 2038
ATG GCA GCC CCC TTG TAC CCT CTC ACC AAA ACG GGG ACT CTG TTT AAT TGG GGC CCA GAC
MET Ala Ala Pro Leu Tyr Pro Leu Thr Lys Thr Gly Thr Leu Phe Asn Trp Gly Pro Asp
```

```
                                                                                           2098
CAA CAA AAG GCC TAT CAA GAA ATC AAG CAA GCT CTT CTA ACT GCC CCA GCC CTG GGG TTG
Gln Gln Lys Ala Tyr Gln Glu Ile Lys Gln Ala Leu Leu Thr Ala Pro Ala Leu Gly Leu

2158
CCA GAT TTG ACT AAG CCC TTT GAA CTC TTT GTC GAC GAG AAG CAG GGC TAC GCC AAA GGT
Pro Asp Leu Thr Lys Pro Phe Glu Leu Phe Val Asp Glu Lys Gln Gly Tyr Ala Lys Gly

2218
GTC CTA ACG CAA AAA CTG GGA CCT TGG CGT CGG CCG GTG GCC TAC CTG TCC AAA AAG CTA
Val Leu Thr Gln Lys Leu Gly Pro Trp Arg Arg Pro Val Ala Tyr Leu Ser Lys Lys Leu

2278
GAC CCA GTA GCA GCT GGG TGG CCC CCT TGC CTA CGG ATG GTA GCA GCC ATT GCC GTA CTG
Asp Pro Val Ala Ala Gly Trp Pro Pro Cys Leu Arg MET Val Ala Ala Ile Ala Val Leu

2338
ACA AAG GAT GCA GGC AAG CTA ACC ATG GGA CAG CCA CTA GTC ATT CTG GCC CCC CAT GCA
Thr Lys Asp Ala Gly Lys Leu Thr MET Gly Gln Pro Leu Val Ile Leu Ala Pro His Ala

2398
GTA GAG GCA CTA GTC AAA CAA CCC CCC GAC CGC TGG CTT TCC AAC GCC CGG ATG ACT CAC
Val Glu Ala Leu Val Lys Gln Pro Pro Asp Arg Trp Leu Ser Asn Ala Arg MET Thr His

2458
TAT CAG GCC TTG CTT TTG GAC ACG GAC CGG GTC CAG TTC GGA CCG GTG GTA GCC CTG AAC
Tyr Gln Ala Leu Leu Leu Asp Thr Asp Arg Val Gln Phe Gly Pro Val Val Ala Leu Asn

2518
CCG GCT ACG CTG CTC CCA CTG CCT GAG GAA GGG CTG CAA CAC AAC TGC CTT GAT AAT TCC
Pro Ala Thr Leu Leu Pro Leu Pro Glu Glu Gly Leu Gln His Asn Cys Leu Asp Asn Ser

2530
CGC TTA ATT AAT
Arg Leu Ile Asn
``` or the degenerate variants thereof.

The invention also relates to the vectors containing the gene of the invention, hosts transformed with the vectors of the invention, and the reverse transcriptase expressed by the transformed hosts of the invention.

The invention also relates to a fusion protein comprising a polypeptide having RNA-dependent DNA polymerase activity and substantially no RNase H activity and a second peptide selected from polypeptide proteins which stabilize the fusion protein and hydrophobic leader sequences.

The invention also relates to a method of producing reverse transcriptase having DNA polymerase activity and substantially no RNase H activity, comprising culturing transformed hosts of the invention under conditions which produce reverse transcriptase, and isolating the reverse transcriptase so produced.

The invention also relates to a method of preparing cDNA from mRNA comprising contacting mRNA with a polypeptide having RNA-dependent DNA polymerase activity and substantially no RNase H activity, and isolating the cDNA so produced.

The invention also relates to a kit for the preparation of cDNA from mRNA comprising a carrier being compartmentalized to receive in close confinement therein one or more containers, wherein
(a) a first container contains reverse transcriptase having DNA polymerase activity and substantially no RNase H activity;
(b) a second container contains a buffer and the nucleoside triphosphates;
(c) a third container contains oligo(dT)primer; and
(d) a fourth container contains control RNA.

The invention is related to the discovery that portions of the RT gene can be deleted to give a deletion mutant having DNA polymerase activity but no detectable RNase H activity. This purified mutant RT lacking RNase H activity can be used to effectively synthesize cDNA from mRNA.

DESCRIPTION OF THE FIGURES

FIG. 5. This figure depicts an autoradiogram of $^{32}$P-labeled 2.3 kb poly(A)-tailed RNA after oligo(dT)-primed cDNA synthesis catalyzed by pRTdEcoRV-C RT or pRT601 RT. Aliquots were removed from reaction mixtures containing no enzyme (-E) or 200 units of RT at the times indicated (in min). The minus enzyme control was incubated for 60 min. Samples were electrophoresed as described in Materials and Methods. A 1 kb ladder was used as marker (M).

FIG. 6. This figure depicts the DNA sequence which encodes reverse transcriptase having DNA polymerase activity and substantially no RNase H activity. Also shown is the corresponding amino acid sequence.

DESCRIPTION OF THE PREFERRED EMBODIMENTS

Figure 1:
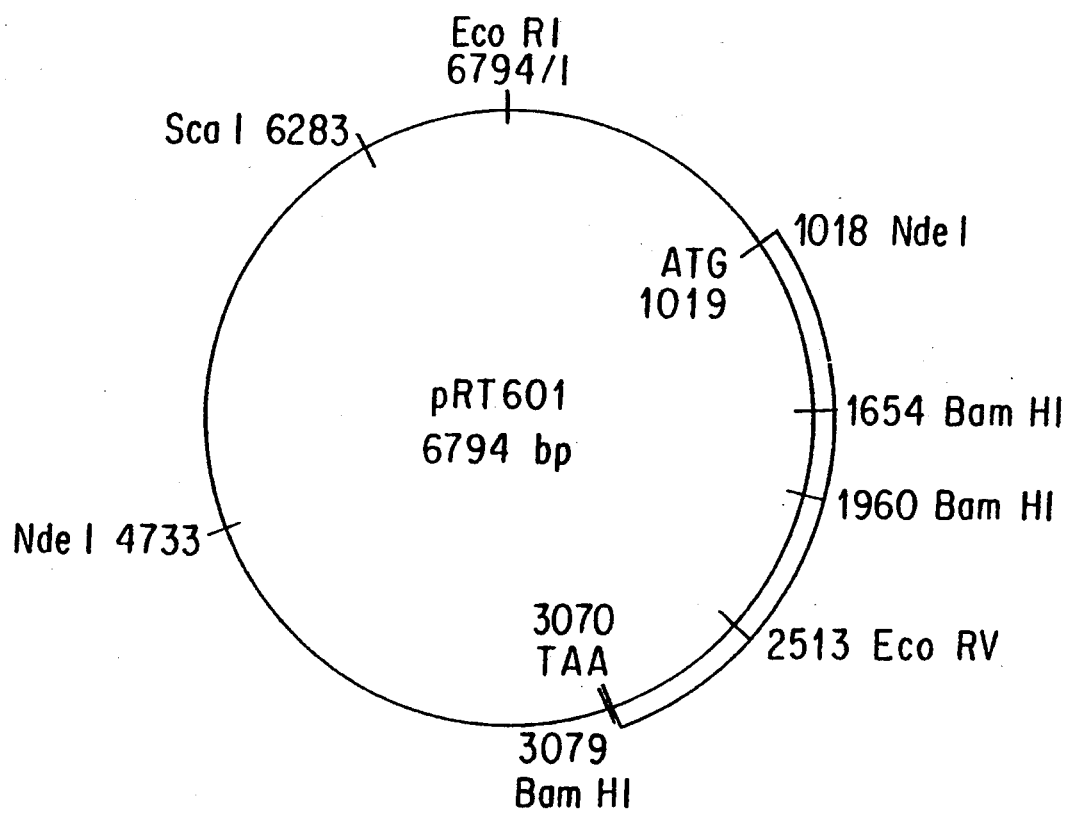
FIG. 1. This figure depicts the restriction map of plasmid pRT601. The M-MLV RT gene extends from position 1,019 to 3,070.

The invention relates to the production of reverse transcriptase having DNA polymerase activity and substantially no RNase H activity, using recombinant DNA techniques.

Recombinant plasmids constructed as described herein provide reverse transcriptase for use in recombinant DNA technology to synthesize cDNA from mRNA without the problem associated with RNase H activity which degrades mRNA template during first-strand synthesis.

By the terms "substantially no RNase H activity" is intended reverse transcriptase purified to near homogeneity and having an RNase H activity of less than 0,001 pmoles $[^3H](A)_n$ solubilized per $\mu$g protein with a $[^3H](A)_n \cdot (dT)_n$ substrate in which the $[^3H](A)_n$ has a specific radioactivity of 2,200 cpm/pmole. RNase H activities of this specific activity or less allows the preparation of cDNA without significant degradation of the mRNA template during first-strand synthesis.

By the terms "degenerate variants" is intended cloned genes having variations of DNA sequence, but which encode the same amino acid sequence.

The reverse transcriptase gene (or the genetic information contained therein) can be obtained from a number of different sources. For instance, the gene may be obtained from eukaryotic cells which are infected with retrovirus, or from a number of plasmids which contain either a portion of or the entire retrovirus genome. In addition, messenger RNA-like RNA which contains the RT gene can be obtained from retroviruses. Examples of sources for RT include, but are not limited to, Moloney murine leukemia virus (M-MLV); human T-cell leukemia virus type I (HTLV-I); bovine leukemia virus (BLV); Rous Sarcoma Virus (RSV); human immunodeficiency virus (HIV); yeast, including Saccharomyces, Neurospora, Drosophila; primates; and rodents. See, for example, Weiss et al,, U.S. Pat. No. 4,663,290 (1987); Gerard, G. R., *DNA* 5:271–279 (1986); Kotewicz, M. L., et al., *Gene* 35:249–258 (1985); Tanese, N., et al., *Proc. Natl. Acad. Sci. (USA)* 82:4944–4948 (1985); Roth, M. J., et al., *J. Biol. Chem.* 260:9326–9335 (1985); Michel, F., et al., *Nature* 316:641–643 (1985); Akins, R. A., et al., *Cell* 47:505–516 (1986), *EMBO J.* 4:1267–1275 (1985); and Fawcett, D. F., *Cell* 47:1007–1015 (1986).

RT proviral DNA can be isolated using standard isolation techniques. The DNA is cleaved into linear fragments, any one of which may contain the genes which encode RT. Such fragmentation can be achieved using enzymes which digest or cleave DNA, such as restriction enzymes which cleave DNA as specific base sequences. After the linear DNA fragments are generated, they are separated according to size by standard techniques. Such recombinant DNA techniques may be performed as described by Maniatis, T., et al, *Molecular Cloning: A Laboratory Manual,* Cold Spring Harbor Laboratory, Cold Spring Harbor N.Y. (1982)

Identification of the DNA fragment which contains the gene may be accomplished in a number of ways. For example, it is possible to sequence the DNA fragments (Maxam and Gilbert, *Methods in Enzymology* 64:499 (1980); Messing, J., *Meth. in Enz.* 101C:20 (1983)) to identify which fragment contains the reverse transcriptase gene. Alternatively, hybridization techniques (Southern, *J. Mol, Biol.* 98:503 (1975)) using a labeled (e.g., radioactively labeled) DNA probe may be employed.

The fractions containing the desired DNA are pooled, ligated into a suitable vector, and used to transform a host. Screening for transformed hosts containing the RT gene may be accomplished by, for example, the method disclosed by Gerard et al., *Biochem.* 13:1632–1641 (1974) or by Gerard et al., *J. Virol.* 15:785–797 (1975). Alternatively, clones containing reverse transcriptase may be identified by hybridization with complementary labeled DNA.

An alternative to isolating the reverse transcriptase gene from a retroviral proviral DNA is to make cDNA to the mRNA-like RNA which codes for reverse transcriptase. To this end, mRNA-like RNA coding for reverse transcriptase is isolated from retrovirus. By standard techniques, the isolated mRNA is then converted into cDNA using reverse transcriptase. The cDNA can then be inserted into a plasmid vector in a conventional manner.

The choice of a suitable vector depends on a number of considerations known to one of ordinary skill in the art, such as the size of the fragment, nature of the host, number and position of restriction sites desired, and the selection marker and markers desired. Such vectors may include replicon and control sequences from species compatible with a host cell (see Maniatis et al., supra). Expression of the RT genes may also be placed under control of other regulatory sequences homologous or heterologous to the host organism in its untransformed state. For example, lactose-dependent *E. coli* chromosomal DNA comprises a lactose or lac operon which mediates lactose utilization by elaborating the enzyme $\beta$-galactosidase. The lac control elements may be obtained from bacteriophage lambda plac 5, which is infectious for *E. coli.* The lac promoter-operator system can be induced by IPTG.

Other promoter-operator systems or portions thereof can be employed as well. For example, galactose, alkaline phosphatase, tryptophan, xylose, tac, lambda pL, lambda pR and the like can be used. Once the vector or DNA sequence containing the constructs has been prepared, the vectors may be introduced into an appropriate host. Various techniques may be employed such as protoplast fusion, $CaCl_2$, calcium phosphate precipitation, electroporation, or other conventional DNA transfer techniques. The vectors may then be introduced into a second host by similar transfer methods, and also by cell to cell transfer methods such as conjugation. This cell-to-cell transfer may be accomplished using known techniques which depend upon the nature of the transferer bacterium, the recipient bacterium, and the cloning vector used to propagate the RT DNA. The transfer may require the use of a helper plasmid. See, for example, Ditta, G., et al., *Proc. Natl. Acad. Sci. (USA)* 77:7347–7351 (1980).

RT genes having DNA polymerase activity and substantially no RNase H activity may be obtained by deletion of deoxyribonucleotides at the 3' end of the gene which encode the portion of the polypeptide having RNase H activity. Deletions of the RT gene may be accomplished by cutting the plasmid at selected restriction sites within the RT gene and discarding the excised fragment. Further deletion of consecutive deoxyribonucleotides may be accomplished by treating the fragment with an exonuclease. The DNA ends may then be joined in such a way that the translation reading frame of the gene is maintained. The plasmid thus obtained may then be used to transform hosts which may then be screened for altered RT activity. RT RNase H activity may be assayed according to Gerard et al., *J, Virol.* 15:785–797 (1975). DNA polymerase activity may be assayed according to Gerard et al., *Biochem.* 13:1632–1641 (1974). Clones having DNA polymerase activity and substantially no RNase H activity may be used to prepare RT with altered activity.

According to these methods, the portion of the RT gene derived from M-MLV which encodes DNA polymerase was localized to about 1495 base pairs (about 1018 to about 2512) as shown in FIG. 6. The protein expressed by this gene has about 503 amino acids (FIG. 6). This protein has DNA polymerase activity and substantially no RNase H activity.

The invention also relates to fusion proteins which comprise the reverse transcriptase of the invention. Such fusion proteins may comprise, for example, a carrier protein which has a leader sequence of hydrophobic amino acids at the amino terminus of the reverse transcriptase. This carrier protein is normally excreted through the membrane of the cell within which it is made. By cleavage of the hydrophobic leader sequence during excretion, a means is provided for producing reverse transcriptase which can be recovered either from the periplasmic space or the medium in which the bacterium is grown. The use of such a carrier protein allows isolation of reverse transcriptase without contamination by other proteins within the bacterium, and achieves production of a form of reverse transcriptase having greater stability by avoiding the enzymes within the bacterial cell which degrade foreign proteins. The DNA and amino acid sequences for such hydrophobic leader sequences, as well as methods of preparing such fusion proteins are taught, for example, by Gilbert et al., U.S. Pat. No. 4,411,994 (1983).

It is also possible to prepare fusion proteins comprising the reverse transcriptase of the invention which is substituted at the amino or carboxy termini with polypeptides which stabilize or change the solubility of the reverse transcriptase. An amino-terminal gene fusion which encodes reverse transcriptase, having both DNA polymerase and RNase activity, and trpE taught, for example, by Tanese, N. et al., *Proc. Nat'l. Acad. Sci.* 82:4944–4948 (1985). A carboxy-terminal gene fusion which encodes reverse transcriptase and part of the plasmid pBR322 tet gene is taught, for example, by Kotewicz, M., et al., *Gene* 35:249–258 (1985) and Gerard, G., *DNA* 5:271–279 (1986).

The transformed hosts of the invention may be cultured under protein producing conditions according to any of the methods which are known to those skilled in the art.

The reverse transcriptase having DNA polymerase activity and substantially no RNase activity may be isolated according to conventional methods known to those skilled in the art. For example, the cells may be collected by centrifugation, washed with suitable buffers, lysed, and the reverse transcriptase isolated by column chromatography, for example, on DEAE-cellulose, phosphocellulose (see Kotewicz et al., *Gene* 35:249–258 (1985)) or other standard isolation and identification techniques using, for example, polyribocytidylic acid-agarose, or hydroxylapatite or by electrophoresis or immunoprecipitation.

The reverse transcriptase so produced may be used to prepare cDNA from RNA by, for example, hybridizing an oligo(dT) primer or other complementary primers with the mRNA. The synthesis of a complete cDNA may be accomplished by adding the reverse transcriptase and all four deoxynucleoside triphosphates. Using the reverse transcriptase produced by the present invention allows for the preparation of cDNA from mRNA without concomitant degradation of the mRNA which results in incomplete cDNA synthesis. The resulting RNA-DNA hybrid may be treated, for example, with alkali or RNase H to selectively hydrolyze the RNA to leave cDNA which may be converted to double-stranded form in a second DNA reaction catalyzed by reverse transcriptase or other DNA polymerase. See Old, R. W., et al., *Principals of Gene Manipulation,* second edition, Studies in Microbiology, Vol. 2, University of California Press, p. 26 (1981).

The reverse transcriptase of the invention is ideally suited for incorporation into a kit for the preparation of cDNA from RNA. Such a kit may comprise a carrier means being compartmentalized to receive a close confinement therein, one or more container means, such as vials, tubes, and the like, each of said container means comprising one of the separate elements of the method used to prepare cDNA from RNA. For example, there may be provided a container means containing reverse transcriptase having DNA polymerase activity and substantially no RNase H activity, in solution. Further container means may contain suitable buffers, substrates for DNA synthesis such as the deoxynucleoside triphosphate, oligo(dT) primer, and control RNA for use as a standard.

The reverse transcriptase may be present in the solution at a concentration of 200 units/ml to 400 units/ml. The deoxynucleoside triphosphases may be present either in lyophilized form or as part of a buffer at a concentration of 0.5 mM to 2 mM. A suitable buffer, present at 5 times the final concentration of use, includes 250 mM Tris-HCl (pH 7.5 to 8.3), 375 mM KCl, 15 mM MgCl$_2$, and 50 mM dithiothreitol. The oligo (dT) may be present at a concentration of 5 $\mu$g/ml to 20 $\mu$g/ml. Control RNA, such as 2.3 kb control RNA, may be present at a concentration of 10 $\mu$g/ml to 20 $\mu$g/ml.

The following examples are illustrative but not limiting of the methods and compositions of the present invention. Any suitable modifications and adaptations which are obvious to one of ordinary skill in the art in recombinant DNA techniques are within the spirit and scope of the present invention.

EXAMPLES

MATERIALS AND METHODS

Plasmids and Bacterial Strains

For deletion analysis of RT, a clone of M-MLV RT was constructed to overproduce stable RT in *Escherichia coli,* pRT601 (FIG. 1). Gerard, G. F., et al., *DNA* 5:271–279 (1986). It is a pBR322 replicon containing the strong lambda leftward promoter, pL, and the ribosome binding site of the lambda cII gene. (Higher copy number derivatives of pBR322, such as pUC plasmids, can also be used.) The coding sequence for the RT gene was carefully engineered into this plasmid to produce a protein with the amino terminus of the viral protein, and a carboxy terminus similar to the viral enzyme. Gerard, G. F., supra.

Two bacterial strains were used to propagate clones and express RT: K802 (Maniatis, T., et al., (1982), *Molecular Cloning: A Laboratory Handbook,* pp. 504–505, Cold Spring Harbor Laboratory, Cold Spring Harbor, N.Y.), made lysogenic for lambda cIindlts857 Sam7, and N4830 (Gottesman, M. E., et al., *J. Mol. Biol.* 140:57–75 (1980)), which contains a deleted a cryptic lambda prophage expressing the temperature sensitive cI allele indltS857. Bacteria were grown in super broth (SB) containing 2% tryptone, 1% yeast extract, 0.1% NaCl, pH 7.5, and 50 μg/ml ampicillin.

Plasmid Construction

Standard procedures for plasmid construction were performed as described previously (Kotewicz, M. L., et al., *Gene* 35:249–258 (1985); Gerard, G. F., et al., *DNA* 5:271–279 (1986)).

Temperature Induction of *E. coli* Carrying pRT601 and Its Derivatives

Cultures of bacteria were grown in SB broth overnight at 32° C. and diluted 1:20 in fresh SB in the morning. The cells were grown at 32° C. until the $A_{590}$ was 0 8, and were induced by swirling in a 65° C. water bath until the temperature reached 42° C. Induction was continued for 30 minutes in a shaking water bath at 42° C., and then the cultures were incubated at 37° C. and grown an additional 30 minutes.

Preparation of Cell Extracts

Unless otherwise noted, all operations were performed at 4° C. Pelleted cells from one ml of culture were washed, lysed, and centrifuged as described previously (Kotewicz, M. L., supra). Supernatants were removed and assayed for RNase H and DNA polymerase activity.

Enzymes Assays

RT DNA polymerase activity in extracts was assayed specifically by using poly(2'-O-methylcytidylate)-oligodeoxyguanylate [$(Cm)_n \cdot (dG)_{12-18}$] (Gerard, G. F., et al., *DNA* 5:271–279 (1986), eliminating interference from cellular DNA polymerases. To establish DNA polymerase specific activities of purified RT preparations, activity was assayed with $(A)_n \cdot (dT)_{12-18}$ (Houts, G. E., et al., *J. Virol.* 29:517–522 (1979) as described by Gerard, G. F., et al., *DNA* 5:271–279 (1986). One unit of DNA polymerase activity is the amount of enzyme that incorporates one nmole of deoxynucleoside monophosphate into acid insoluble product at 37° C. in 10 min.

RNase H activity in crude extracts and purified enzyme was assayed in reaction mixtures (50 μl) containing 50 mM Tris-HCl (pH 8.3), 2 mM $MnCl_2$, mM dithiothreitol and [$^3$H]$(A)_n \cdot (dT)_n$ (5 μM [$^3$H]$(A)_n$, 35 cpm/pmole; 20 μM $(dT)_n$). Reactions were incubated at 37° C. for 20 min and were stopped by adding 10 μl of tRNA (1 mg/ml) and 20 μl of cold 50% TCA. After 10 minutes on ice, the mixture was centrifuged for 10 minutes in an Eppendorf centrifuge. Forty μl of the supernatant was counted in aqueous scintillant. One unit of RNase H activity is the amount of enzyme required to solubilize one mole of [$^3$H]$(A)_n$ [$^3$H]$(A)_n \cdot (dT)_n$ in 10 min at 37° C.

Synthesis of Poly(A)-Tailed RNA

Synthetic 2.3 kb and 6.2 kb RNAs containing a 19 nucleotide poly(A) tail at the 3' end were synthesized with T7 RNA polymerase from Xba I-cut pJD2.3 and Hind III-cut pHL3X, respectively. Reaction mixtures (0.3 ml) contained 40 mM Tris-HCl (pH 8.0), 8 mM $MgCl_2$, 2 mM spermidine-HCl, 5 mM dithiothreitol, 0.4 mM each of CTP, UTP, GTP, and ATP, 20 μg/ml DNA, and 2,000 units/ml T7 RNA polymerase. Uniformly labeled RNA was synthesized with all four [α-$^{32}$P]NTPs, each at 0.4 mM and 250 cpm/pmole. After 1 hr incubation at 37° C., the RNA product was phenol extracted, ethanol precipitated, and purified by oligo(dT)-cellulose chromatography to ensure the presence of a poly(A) tail.

Conditions for cDNA Synthesis

When assessing the effect of cDNA synthesis upon the integrity of template RNA, reaction mixtures (50 μl) contained 50 mM Tris-HCl (pH 8.3), 75 mM KCl, 3 mM $MgCl_2$, 10 mM dithiothreitol, 0.5 mM each dATP, dGTP, and dTTP 0.5 mM [$^3$H]dCTP (200 cpm/pmol), 50 μg/ml $(dT)_{12-18}$, 20 μg/ml 2.3 kb [$^{32}$P]labeled RNA, and 4,000 units/ml RT. The reactions were incubated at 37° C. and duplicate 2.5 μl aliquots were removed at 0, 1, 5, 10, 30, and 60 min. One aliquot was precipitated onto glass fiber filters using TCA to determine the amount of cDNA synthesized, and the other aliquot was prepared for glyoxal gel analysis. Carmichael, G. G., et al., *Method Enzymol.* 65:380–391 (1980). The glyoxalated RNA was fractionated on a 1% agarose gel, dried, and autoradiographed. In some cases, 10 units of *E. coli* RNase H were added to the reaction mixture after 60 min and the incubation continued for 10 more min before aliquots were taken.

When measuring the ability of RT to synthesize a cDNA copy of long RNA, reaction mixtures (10 μl) contained the same buffer and salts, 0.5 mM each of dATP, dGTP, dTTP, and [α-$^{32}$P]dCTP (600 cpm/pmole), 50 μg/ml actinomycin D, 50 μg/ml $(dT)_{12-18}$, 100 μg/ml 6.2 kb poly (A)-tailed RNA, and 20,000 units/ml RT. After 1 hr at 37° C., the product in an aliquot (1 μl) was precipitated with TCA, counted, and the remaining DNA size fractionated on an alkaline 1.4% agarose gel according to McDonnel, M. W. et al., *J. Mol. Biol.* 110:119–146 (1977).

Purification of RT

Cells were grown to an $A_{590}$ of 3 in TYN and ampicillin medium (Gerard, G. F., et al., *DNA* 5:271–279 (1986)) at 30° C., induced at 43° C. for 45 min, and then grown at 36° C. for 3.5 hr before harvesting. RT was extracted from 100 g of cells as described (Gerard, G. F., supra) with the following exceptions. RT was precipitated by addition of solid $(NH_4)_2SO_4$ to 40% saturation. The $(NH_4)_2SO_4$ pellet was dissolved in 50 ml of 20 mM Tris-HCl (pH 7.5), 1 mM EDTA, 0.1 M NaCl, 5% glycerol, 1 mM dithiothreitol, and 0.01% n-octyl-β-D-glucopyranoside, the suspension was clarified by centrifugation at 10,000×g for 10 min, and the supernatant was desalted on a 320 ml (5×16 cm) Sephadex G-25 column run in buffer A (20 mM Tris-HCl, pH 7.5, 1 mM dithiothreitol, 1 mM EDTA, 5% glycerol, 0.01% NP-40) plus 0.1 M NaCl. After phosphocellulose chromatography, the RT peak was pooled, diluted with an equal volume of buffer A, and chromatographed on a 21-ml heparin-agarose column (1.5×12 cm) equilibrated in buffer A plus 0.1 M NaCl. The RT peak from the heparinagarose column was chromatographed on a Mono-S HR 5/5 column equilibrated in buffer A (Gerard, G. F., supra).

RESULTS

Construction of Reverse Transcriptase Gene Deletions

Figure 2:
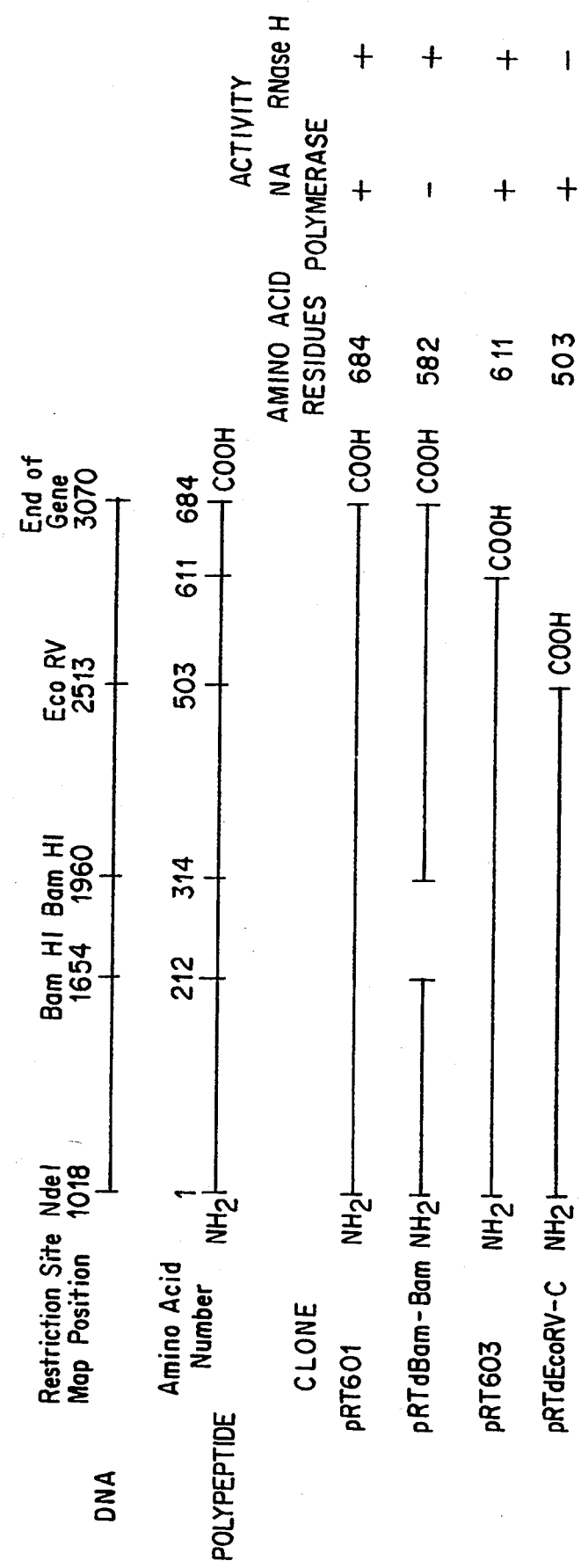
FIG. 2. This figure depicts schematic representation of pRT601 and related plasmids, and the enzymatic activities and predicted structure of the M-MLV RT protein coded by each plasmid.

Deletions of the M-MLV RT gene were constructed by cutting pRT601 (FIG. 1) at selected restriction sites within the RT gene, discarding the excised fragment, and joining the DNA ends in such a way that the translation reading frame of the gene was maintained. pRTdBam-Bam was constructed by deleting the Bam HI fragment between nucleotide positions 1,654 and 1,960 (FIGS. 1 and 2). Ligation of the Bam HI half sites at positions 1,654 and 1,960 maintained the translation reading frame across the site.

A deletion at the carboxy terminus of M-MLV RT (pRTdEcoRV-C) was constructed by deleting all of the 3' end of the gene downstream of the Eco RV site at position 2,513 (FIGS. 1 and 2). To construct pRTdEcoRV-C, a Sca I (position 6,238) to Eco RV (position 2,513) fragment of pRT601 containing the 5' portion of the RT gene was ligated to a Sca I-Eco RI fragment derived from plasmid pBRT (Gerard, G. F., supra). The 3,211 base pair pBRT Sca I-ECo RI fragment contained the pBR322 origin of replication and a universal translation terminator sequence just inside the Eco RI site. The Eco RI site was repaired with DNA polymerase I Klenow fragment before ligation.

The plasmid of pRTdEcoRV-C was deposited in *E. coli* under the terms of the Budapest Treaty at the American Type Culture Collection (ATCC), Rockville, Md., and given accession number 67555.

pRT603 was constructed as described (Gerard, G. R., supra) which encodes an RT that contains 73 fewer amino acids than pRT601, all deleted from the carboxy terminus (FIG. 2).

DNA Polymerase and RNase H Levels in Cells Bearing Deletion Plasmids

Alteration of as little as 3 amino acids at the carboxy end of M-MLV RT can influence markedly the stability of the protein in *E. coli* (Gerard, G. F. Supra). This must be taken into consideration in making correlations between cloned RT deletions and enzymatic activities in *E. coli* extracts. Both DNA polymerase and RNase H activity must be assayed and relative enzyme levels compared. For example, pRT603 codes for an RT with 73 fewer amino acids at the carboxy terminus than pRT601 RT (Gerard, G. F., supra; FIG. 2). The level of DNA polymerase activity in *E. coli* extracts of pRT603 RT is reduced 5 fold relative to pRT601 (Gerard, G. F. supra). However, the DNA polymerase and RNase H specific activities of purified pRT601 and pRT603 RT are comparable (Table 2). The reduced DNA polymerase activity in *E. coli* extracts of pRT603 RT is not due to a selective effect of the deletion on DNA polymerase activity, but rather to a reduction in the stability of pRT603 RT relative to pRT601 RT in cells ($t_{\frac{1}{2}}$ of 7 min versus 33 min) (Gerard, G. F. supra). Therefore, deletions within 70 amino acids of the RT carboxy terminus do not affect either RNase H or DNA polymerase activity.

In contrast, the DNA polymerase activity of pRTdBam-Bam RT was eliminated totally without affecting RNase H activity (Table 1) by the deletion of 102 amino acid residues between amino acids 212 and 314 (FIG. 2). Introduction of a more extensive deletion of 180 amino acids at the carboxy end of RT in pRTdEcoRV-C RT (FIG. 2) yielded extracts with RT DNA polymerase levels unchanged compared to pRT601 extracts, but with RNase H levels reduced 7.5 fold (Table 1). The residual RNase H activity in pRTdEcoRV-C extracts could be due to *E. coli* RNase H, the 5'→3' exonuclease of DNA polymerase I, or a small amount of residual RT-coded RNase H activity To resolve this issue, pRTdEcoRV-C RT was purified and compared to RT encoded by pRT601.

Purification and Properties of pRTdEcoRV-C RT

Figure 3:
FIG. 3. This figure depicts an SDS-polyacrylamide gel of M-MLV RT. pRTdEcoRV-C RT (A) and pRT601 RT (B) (3 μg of each) were run on an SDS 10% polyacrylamide gel (Laemmli, U. K., Nature 227:680–685 (1970)). The gel was stained with Coomassie blue. Lane M contained Mr standards.

M-MLV reverse transcriptase encoded by pRTdEcoRVC, pRT601, and pRT603 were purified as described in Materials and Methods. A summary of the purification of pRTdEcoRV-C RT is presented in Table 3. Three column steps produced a nearly homogeneous mutant enzyme with the same DNA polymerase specific activity as pRT601 RT with the template-primer $(Cm)_{n'} \cdot (dG)_{12-18}$ (Table 2). With $(A)_{n'} \cdot (dT)_{12-18}$, the mutant enzyme had one-fourth the DNA polymerase activity of pRT601 RT (Table 2). RNase H activity of purified pRTdEcoRV-C RT was undetectable using $[^3H](A)_{n'} \cdot (dT)_n$ as the substrate. Most RNase H activity in extracts was eliminated from mutant RT by precipitation of the enzyme with 40% $(NH_4)_2SO_4$ (Table 3). Under these conditions, DNA polymerase I remains soluble (Richardson, C., et al., *J. Biol. Chem.* 239:222–230 (1964)), as does most of the RNase H activity in the extract. As judged by SDS-polyacrylamide gel electrophoresis, pRTdEcoRV-C RT purified through the Mono-S column was greater than 90% pure and had a molecular weight of 56,000 (FIG. 3), consistent with the molecular weight (57,000) predicted by the DNA sequence.

Figure 4:
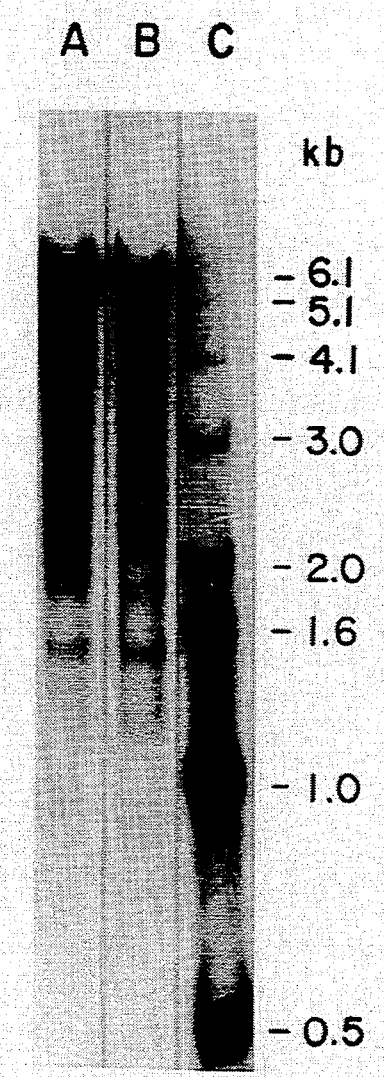
FIG. 4. This figure depicts an autoradiogram of $^{32}$P-labeled cDNA synthesized from 6.2 kb RNA (Materials and Methods) by pRTdEcoRV-C RT (A) or pRT601 RT (B). A 1 kb ladder was used as a standard (C). Electrophoresis was performed on an alkaline 1.4% agarose gel (McDonnel, M. W., et al., J. Mol. Biol. 110:119–146 (1977)).

A number of enzymatic properties of purified pRTdEcoRV-C RT and pRT601 RT were compared and were found to be similar. These included half life at 37° C., monovalent and divalent metal ion optima, fidelity of dNTP incorporation with homopolymer templates, and insensitivity to stimulation by polyanions. The abilities of the two enzymes to synthesize heteropolymeric DNA were also compared. FIG. 4 shows that pRTdEcoRV-C RT catalyzed the synthesis of full-length cDNA from 6.2 kb RNA more efficiently than pRT601 RT. The amount of cDNA synthesized from 1 μg of RNA was 0.28 μg (34% full-length) and 0.24 μg (24% full-length) with pRTdEcoRV-C RT and pRT601 RT, respectively.

To confirm that pRTdEcoRV-C RT completely lacked RNase H activity, the integrity of a uniformly $^{32}P$-labeled RNA template after conversion to hybrid form during RT-catalyzed DNA synthesis was examined. FIG. 5 shows that with pRT601 RT, the full-length 2.3 kb RNA template was degraded totally after 5 min of synthesis. In contrast, with pRTdEcoRV-C RT the RNA was intact even after 60 min. The amount of cDNA synthesized after 60 min from 1 μg of RNA was 0.67 and 0.76 μg with pRT601 and pRTdEcoRV-C RT, respectively. When 10 units of *E. coli* RNase H were added to the pRTdEcoRV-C RT reaction after 60 min of incubation, all of the RNA was degraded, confirming the hybrid state of the RNA. In addition, 15 μg (1,200 units) of pRTdEcoRV-C RT solubilized no radioactivity from a $[^3H](A)_{n'} \cdot (dT)_n$ substrate in which the $[^3H](A)_n$ had a specific activity of 2,200 cpm/pmole (Materials and Methods).

Experiments with a frameshift mutant of MLV producing a 47K RT molecule truncated at the carboxy terminus (Levin, J. G. et al., *J. Virol.* 51:470–478 (1984))

and with antibodies to synthetic peptides modeled to Rous sarcoma virus pol gene sequences (Grandgenett, D. et al., *J. Biol. Chem.* 260:8243-8249 (1985)) suggest the RNase H activity of RT resides within the amino-terminal portion of the molecule. Conversely, the extensive homology found between the amino acids of *E. coli* RNase H and the 153-residue segment at the carboxy-terminal end of M-MLV RT (Johnson, M. S. et al. *Proc. Natl. Acad. Sci (USA)* 83:7648-7652 (1986)) suggests the RNase H activity resides within the carboxy-terminal portion of RT.

By deleting large segments (100 to 200 codons) of the M-MLV RT gene, the regions within the RT molecule responsible for DNA polymerase and RNase H activity have been identified. DNA polymerase was mapped to the amino half of the molecule, and RNase H to within 200 amino acids of the carboxy end, confirming the predictions based upon amino acid homology (Johnson, M. S. et al., supra). In this context, the results with one RT clone, pRT603 (FIG. 2), are of interest. The RT protein encoded by pRT603 is missing the carboxy half of the 153 amino acid segment of RT homologous to *E. coli* RNase H, which includes 20 of 48 homologous amino acids. Yet, pRT603 RT has normal levels of RNase H activity. These missing, homologous residues apparently are not required for catalysis, and might serve a nucleic acid binding or structural role. Consistent with the latter, a single amino acid change at a position 12 residues from the carboxy end of *E. coli* RNase H produces a 10-fold reduction in RNase H specific activity (Kanaya, S. et al., *J. Bacteriol.* 154:1021-1026 (1983)). This reduction appears to be the result of altered protein conformation (Kanaya, S. et al., supra).

If the RT polymerase and nuclease active sites reside on separate structural domains, it should be possible theoretically to isolate two separate protein fragments, each with a single activity. A 24 K to 30 K proteolytic fragment of RT possessing only RNase H activity has been isolated (Lai, M. H. T. et al., *J. Virol.* 25:652-663 (1978); Gerard, G. F., *J. Virol.* 26:16-28 (1978); Gerard, G. F., *J. Virol.* 37:748-754 (1981)), but unfortunately, the location of this RNase H fragment in the parent RT polypeptide has not been established, and no analogous DNA polymerase containing fragment has ever been found. The results presented here show that of the 684 amino acids in pRT601 RT, residues between amino acid 212 and 314 are required for DNA polymerase activity, and residues between amino acid 503 and 611 are required for RNase H activity. They also demonstrate for the first time that the RT DNA polymerase activity can exist independently of RNase H activity on an RT protein fragment. Purified pRTdEcoRV-C RT appeared to be totally devoid of RNase H activity, based upon two sensitive assays, and to have full DNA polymerase activity. However, these results do not rule out the possibility that the two active centers share a portion(s) of the RT molecule.

Demonstration of a separate structural domain for the RNase H active center was attempted by constructing two amino-terminal deletion derivatives of pRT601. The first derivative contained sequences for the Eco RV site at position 2513 to the 3' end of the RT gene (see FIG. 2), and the second contained sequences from an Nco I site at position 2302 to the 3' end of the RT gene. Unfortunately, neither clone produced detectable RNase H activity in *E. coli* crude extracts. Such negative results are difficult to interpret because the proteins might be unable to fold in an active form, or might be extremely labile.

Deletion of the carboxy-terminal one-fourth of the M-MLV RT molecule did not disrupt the ability of the protein to fold in an active conformation. pRTdEcoRV-C RT copied heteropolymeric RNA more efficiently than intact RT. Yields of cDNA from 1 μg of 2.3 kb and 6.2 kb RNA were 0.76 μg (50% full-length) and 0.28 μg (34% full-length), respectively. Also, the truncated and intact enzymes had the same DNA polymerase specific activity with $(Cm)_n \cdot (dG)_{12-18}$. However, the truncated enzyme copied $(A)_n \cdot (dT)_{12-18}$ only one fourth as efficiently as the parent RT. The origin of this difference has not yet been established.

TABLE 1

DNA polymerase and RNase H activity in extracts of heat induced *E. coli* K802 (lambda) bearing pRT601 or one of its derivatives.

| Plasmid | DNA polymerase Activity[a] (cpm incorporated/2.5 μl extract) | RNase H Activity[b] (cpm solubilized/2.5 μl extract) |
|---|---|---|
| pRT601 | 10,977 | 2,020 |
| pRTdBam-Bam | 179 | 1,564 |
| pRTdEcoRV-C | 10,038 | 268 |

[a]Reverse transcriptase DNA polymerase activity was assayed with $(Cm)_n \cdot (dG)_{12-18}$ (Materials and Methods).
[b]RNase H activity was assayed with $[^3H](A)_n \cdot (dT)_n$ (Materials and Methods).

TABLE 2

Comparison of activities of purified RT coded by pRT601, pRT603, and pRTdEcoRV-C

| Enzyme | DNA Polymerase Activity with | | RNase H Activity (Units/mg) |
|---|---|---|---|
| | $(Cm)_n \cdot (dG)_{12-18}$ (Units/mg) | $(A)_n \cdot (dT)_{12-18}$ (Units/mg) | |
| pRT601 | 21,700 | 350,000 | 2,670 |
| pRT603 | ND[a] | 230,000 | 1,100 |
| pRTdEcoRV-C | 17,500 | 81,000 | —[b] |

[a]ND, not determined
[b]No activity was detected

TABLE 3

Summary of the purification of pRTdEcoRV-C RT

| | | DNA Polymerase Activity[a] | | | RNase H Activity | | |
|---|---|---|---|---|---|---|---|
| Fraction | Total Protein[c] (mg) | Total (Units) ×10³ | Specific Activity (Units/mg) ×10³ | Yield (%) | Total (Units) ×10³ | Specific Activity (Units/mg) ×10³ | Yield (%) |
| Crude lysate | 7,913 | 255 | 0.03 | 100 | 80 | 0.01 | 100 |
| Polymin P Supernatant | 2,735 | 323 | 0.12 | 127 | 157 | 0.06 | 196 |
| $(NH_4)_2SO_4$ pellet | 63 | 168 | 1.38 | 66 | 6.0 | 0.10 | 7 |
| Phosphocellulose pool | 8.8 | 167 | 19.0 | 66 | 2.0 | 0.23 | 3 |

TABLE 3-continued

Summary of the purification of pRTdEcoRV-C RT

| Fraction | Total Protein[c] (mg) | DNA Polymerase Activity[a] | | | RNase H Activity | | |
|---|---|---|---|---|---|---|---|
| | | Total (Units) ×10³ | Specific Activity (Units/mg) ×10³ | Yield (%) | Total (Units) ×10³ | Specific Activity (Units/mg) ×10³ | Yield (%) |
| Heparin-agarose pool | 6.5 | 111 | 17.1 | 44 | —[b] | — | — |
| Mono S pool | 3.1 | 55 | 17.5 | 22 | —[b] | — | — |

[a] DNA polymerase activity was assayed with $(Cm)_n \cdot (dG)_{12-18}$
[b] No activity could be detected
[c] Protein concentrations were determined using bovine serum albumin as standard according to Lowry, O.H., et al., J. Biol. Chem. 239:222-230 (1964).

What is claimed is:

1. An isolated DNA compound comprising a DNA sequence encoding a polypeptide having DNA polymerase activity and substantially no RNase H activity wherein said polypeptide may be used for the preparation of full length cDNA without significant degradation of the mRNA template during first strand synthesis wherein said DNA compound is derived from an organism selected from the group consisting of a retrovirus, yeast, Neurospora, Drosophila, primates and rodents.

2. The DNA compound of claim 1, wherein said organism is a retrovirus selected from the group consisting of Moloney murine leukemia virus (M-MLV), human T-cell leukemia virus type I (HTLV-I), bovine leukemia virus (BLV), Rous sarcoma virus (RSV)and human immunodeficiency virus (HIV).

3. The DNA compound of claim 1, wherein said organism is M-MLV, comprising the following DNA sequence:

```
                                                                          1078
ATG ACC CTA AAT ATA GAA GAT GAG CAT CGG CTA CAT GAG ACC TCA AAA GAG CCA GAT GTT

1138
TCT CTA GGG TCC ACA TGG CTG TCT GAT TTT CCT CAG GCC TGG GCG GAA ACC GGG GGC ATG

1198
GGA CTG GCA GTT CGC CAA GCT CCT CTG ATC ATA CCT CTG AAA GCA ACC TCT ACC CCC GTG

1258
TCC ATA AAA CAA TAC CCC ATG TCA CAA GAA GCC AGA CTG GGG ATC AAG CCC CAC ATA CAG

1318
AGA CTG TTG GAC CAG GGA ATA CTG GTA CCC TGC CAG TCC CCC TGG AAC ACG CCC CTG CTA

1378
CCC GTT AAG AAA CCA GGG ACT AAT GAT TAT AGG CCT GTC CAG GAT CTG AGA GAA GTC AAC

1438
AAG CGG GTG GAA GAC ATC CAC CCC ACC GTG CCC AAC CCT TAC AAC CTC TTG AGC GGG CTC

1498
CCA CCG TCC CAC CAG TGG TAC ACT GTG CTT GAT TTA AAG GAT GCC TTT TTC TGC CTG AGA

1558
CTC CAC CCC ACC AGT CAG CCT CTC TTC GCC TTT GAG TGG AGA GAT CCA GAG ATG GGA ATC

1618
TCA GGA CAA TTG ACC TGG ACC AGA CTC CCA CAG GGT TTC AAA AAC AGT CCC ACC CTG TTT

1678
GAT GAG GCA CTG CAC AGA GAC CTA GCA GAC TTC CGG ATC CAG CAC CCA GAC TTG ATC CTG

1738
CTA CAG TAC GTG GAT GAC TTA CTG CTG GCC GCC ACT TCT GAG CTA GAC TGC CAA CAA GGT

1798
ACT CGG GCC CTG TTA CAA ACC CTA GGG AAC CTC GGG TAT CGG GCC TCG GCC AAG AAA GCC

1858
CAA ATT TGC CAG AAA CAG GTC AAG TAT CTG GGG TAT CTT CTA AAA GAG GGT CAG AGA TGG

1918
CTG ACT GAG GCC AGA AAA GAG ACT GTG ATG GGG CAG CCT ACT CCG AAG ACC CTC GAA CAA

1978
CTA AGG GAG TTC CTA GGG ACG GCA GGC TTC TGT CGC CTC TGG ATC CCT GGG TTT GCA GAA

2038
ATG GCA GCC CCC TTG TAC CCT CTC ACC AAA ACG GGG ACT CTG TTT AAT TGG GGC CCA GAC
```

-continued

```
                                                             2098
CAA CAA AAG GCC TAT CAA GAA ATC AAG CAA GCT CTT CTA ACT GCC CCA GCC CTG GGG TTG

2158
CCA GAT TTG ACT AAG CCC TTT GAA CTC TTT GTC GAC GAG AAG CAG GGC TAC GCC AAA GGT

2218
GTC CTA ACG CAA AAA CTG GGA CCT TGG CGT CGG CCG GTG GCC TAC CTG TCC AAA AAG CTA

2278
GAC CCA GTA GCA GCT GGG TGG CCC CCT TGC CTA CGG ATG GTA GCA GCC ATT GCC GTA CTG

2338
ACA AAG GAT GCA GGC AAG CTA ACC ATG GGA CAG CCA CTA GTC ATT CTG GCC CCC CAT GCA

2398
GTA GAG GCA CTA GTC AAA CAA CCC CCC GAC CGC TGG CTT TCC AAC GCC CGG ATG ACT CAC

2458
TAT CAG GCC TTG CTT TTG GAC ACG GAC CGG GTC CAG TTC GGA CCG GTG GTA GCC CTG AAC

CCG GCT ACG CTG CTC CCA CTG CCT GAG GAA GGG CTG CAA CAC AAC TGC CTT GAT
``` or the degenerate variants thereof.

4. The DNA compound of claim 1, wherein said organism is M-MLV, comprising the following DNA sequence:

```
                                                             1078
ATG ACC CTA AAT ATA GAA GAT GAG CAT CGG CTA CAT GAG ACC TCA AAA GAG CCA GAT GTT

1138
TCT CTA GGG TCC ACA TGG CTG TCT GAT TTT CCT CAG GCC TGG GCG GAA ACC GGG GGC ATG

1198
GGA CTG GCA GTT CGC CAA GCT CCT CTG ATC ATA CCT CTG AAA GCA ACC TCT ACC CCC GTG

1258
TCC ATA AAA CAA TAC CCC ATG TCA CAA GAA GCC AGA CTG GGG ATC AAG CCC CAC ATA CAG

1318
AGA CTG TTG GAC CAG GGA ATA CTG GTA CCC TGC CAG TCC CCC TGG AAC ACG CCC CTG CTA

1378
CCC GTT AAG AAA CCA GGG ACT AAT GAT TAT AGG CCT GTC CAG GAT CTG AGA GAA GTC AAC

1438
AAG CGG GTG GAA GAC ATC CAC CCC ACC GTG CCC AAC CCT TAC AAC CTC TTG AGC GGG CTC

1498
CCA CCG TCC CAC CAG TGG TAC ACT GTG CTT GAT TTA AAG GAT GCC TTT TTC TGC CTG AGA

1558
CTC CAC CCC ACC AGT CAG CCT CTC TTC GCC TTT GAG TGG AGA GAT CCA GAG ATG GGA ATC

1618
TCA GGA CAA TTG ACC TGG ACC AGA CTC CCA CAG GGT TTC AAA AAC AGT CCC ACC CTG TTT

1678
GAT GAG GCA CTG CAC AGA GAC CTA GCA GAC TTC CGG ATC CAG CAC CCA GAC TTG ATC CTG

1738
CTA CAG TAC GTG GAT GAC TTA CTG CTG GCC GCC ACT TCT GAG CTA GAC TGC CAA CAA GGT

1798
ACT CGG GCC CTG TTA CAA ACC CTA GGG AAC CTC GGG TAT CGG GCC TCG GCC AAG AAA GCC

1858
CAA ATT TGC CAG AAA CAG GTC AAG TAT CTG GGG TAT CTT CTA AAA GAG GGT CAG AGA TGG

1918
CTG ACT GAG GCC AGA AAA GAG ACT GTG ATG GGG CAG CCT ACT CCG AAG ACC CCT CGA CAA

1978
CTA AGG GAG TTC CTA GGG ACG GCA GGC TTC TGT CGC CTC TGG ATC CCT GGG TTT GCA GAA

2038
ATG GCA GCC CCC TTG TAC CCT CTC ACC AAA ACG GGG ACT CTG TTT AAT TGG GGC CCA GAC
```

-continued

```
                                                                                2098
CAA CAA AAG GCC TAT CAA GAA ATC AAG CAA GCT CTT CTA ACT GCC CCA GCC CTG GGG TTG

2158
CCA GAT TTG ACT AAG CCC TTT GAA CTC TTT GTC GAC GAG AAG CAG GGC TAC GCC AAA GGT

2218
GTC CTA ACG CAA AAA CTG GGA CCT TGG CGT CGG CCG GTG GCC TAC CTG TCC AAA AAG CTA

2278
GAC CCA GTA GCA GCT GGG TGG CCC CCT TGC CTA CGG ATG GTA GCA GCC ATT GCC GTA CTG

2338
ACA AAG GAT GCA GGC AAG CTA ACC ATG GGA CAG CCA CTA GTC ATT CTG GCC CCC CAT GCA

2398
GTA GAG GCA CTA GTC AAA CAA CCC CCC GAC CGC TGG CTT TCC AAC GCC CGG ATG ACT CAC

2458
TAT CAG GCC TTG CTT TTG GAC ACG GAC CGG GTC CAG TTC GGA CCG GTG GTA GCC CTG AAC

2518
CCG GCT ACG CTG CTC CCA CTG CCT GAG GAA GGG CTG CAA CAC AAC TGC CTT GAT AAT TCC

2530
CGC TTA ATT AAT
```

5. An isolated DNA compound comprising a DNA sequence which encodes a fusion protein which comprises reverse transcriptase having DNA polymerase activity and substantially no RNase H activity and a second protein comprising a hydrophobic leader peptide or a stabilizing peptide.

6. A vector containing the DNA compound of claim 1 or 5.

7. The vector of claim 6 designated pRTdEcoRV-C which has been deposited at the American Type Culture Collection, Rockville Md. under terms of the Budapest Treaty and given accession number 67555.

8. A host cell transformed with the vector of claim 6.

9. A method of producing reverse transcriptase having DNA polymerase activity and substantially no RNase H activity comprising culturing the transformed host of claim 8 under conditions which produce reverse transcriptase, and isolating the reverse transcriptase so produced.

* * * * *

UNITED STATES PATENT AND TRADEMARK OFFICE
CERTIFICATE OF CORRECTION

PATENT NO. : 5,405,776

DATED : April 11, 1995

INVENTORS : Kotewicz & Gerard

It is certified that an error appears in the above-identified patent and that said Letters Patent is hereby corrected as shown below.

In column 15, lines 29-30, please delete "Rockville, Md." and insert in place thereof --Manassas, VA--.

In column 15, line 30, after "67555." please insert --A Supplemental Deposit of pRTdEcoRV-C in *E. coli* was made under the terms of the Budapest Treaty at the ATCC under accession number PTA-1409.--.

In claim 7, column 24, line 24, please delete "Rockville Md." and insert in place thereof --Manassas, VA,--; and line 25, after "67555" insert --, a Supplemental Deposit of which was made at the ATCC under accession number PTA-1409--.

Signed and Sealed this

Fourteenth Day of November, 2000

*Attest:*

Q. TODD DICKINSON

*Attesting Officer*      *Director of Patents and Trademarks*

US005405776B1

REEXAMINATION CERTIFICATE (3018th)
United States Patent [19]
Kotewicz et al.

[11] B1 5,405,776
[45] Certificate Issued Oct. 1, 1996

[54] CLONED GENES ENCODING REVERSE TRANSCRIPTASE LACKING RNASE H ACTIVITY

[75] Inventors: Michael L. Kotewicz, Columbia; Gary F. Gerard, Frederick, both of Md.

[73] Assignee: Life Technologies, Inc., Gaithersburg, Md.

Reexamination Request:
No. 90/003,804, Apr. 24, 1995

Reexamination Certificate for:
Patent No.: 5,405,776
Issued: Apr. 11, 1995
Appl. No.: 825,260
Filed: Jan. 24, 1992

Related U.S. Application Data

[62] Division of Ser. No. 671,156, Mar. 18, 1991, which is a continuation of Ser. No. 143,396, Jan. 13, 1988, abandoned.

[51] Int. Cl.$^6$ .............. C12N 9/12; C12N 15/48; C12N 15/00; C12N 15/70
[52] U.S. Cl. .......... 435/194; 435/69.1; 435/69.7; 435/172.3; 435/252.3; 435/252.33; 435/320.1; 536/23.2; 536/23.4; 536/23.72; 935/10; 935/14; 935/29; 935/47; 935/66; 935/73; 935/36
[58] Field of Search ............. 435/69.1, 172.3, 435/69.7, 194, 252.3, 252.33, 320.1; 536/23.2, 23.4

[56] References Cited

U.S. PATENT DOCUMENTS 4,795,699 10/1989 Tabor et al. ................. 435/5

OTHER PUBLICATIONS

Zoller, M. A., and Smith, M., 1983, Methods in Enzymology, 100:468–500.
Carter, P., and Wells, J. A., 1987, Science, 237:394–399.
Meloun, B. et al., 1985, FEBS Letters, 183(2):195–200.
Levin, J. G., et al., 1984, Journal of Virology, 51(2):470–478.
Smith, J. K., et al., Journal of Virology, 49(1):200–204, 1984.
Friston, W. I., et al., Journal of Virology, 51(1):26–33, 1984.
Resnick, R., et al., Journal of Virology, 51(3): 813–821, 1984.
Genvin, B. I., et al., Journal of Virology, 31(3):741–751, 1974.
Gorecki and Panet, "Discrimination of DNA Polymerase and RNase H Activities in Reverse Transcriptase of Avian Myeloblastosis Virus," Biochemistry, vol. 17, No. 12, (1978), pp. 2438–2442.
Tanese et al., "Expression of enzymatically active reverse transcriptase in *Escherichia coli*," Proc. Natl. Acad. Sci. USA, vol. 82, No. 15, (Aug. 1985), pp. 4944–4948.
Johnson et al., "Computer analysis of retroviral pol genes: Assignment of enzymatic functions to specific sequences and homologies with nonviral enzymes," Proc. Natl. Acad. Sci. USA, vol. 83, No. 20, (Oct. 1986), pp. 7648–7652.
Shinnick et al., "Nucleotide sequence of Moloney murine leukemia virus," Nature, vol. 293, (Oct. 15, 1981), pp. 543–548.

(List continued on next page.)

*Primary Examiner*—Robert A. Wax

[57] ABSTRACT

The invention relates to a gene which encodes reverse transcriptase having DNA polymerase activity and substantially no RNase H activity. The invention also relates to vectors containing the gene and hosts transformed with the vectors of the invention. The invention also relates to a method of producing reverse transcriptase having DNA polymerase activity and substantially no RNase H activity by expressing the reverse transcriptase genes of the present invention in a host. The invention also relates to a method of producing cDNA from mRNA using the reverse transcriptase of the invention. The invention also relates to a kit for the preparation of cDNA from mRNA comprising the reverse transcriptase of the invention.

OTHER PUBLICATIONS

Tanese et al., "Analysis of Retroviral pol Gene Products with Antisera Raised against Fusion Proteins Produced in *Escherichia coli,*" Journal of Virology, vol. 59, No. 2, (Aug. 1986), pp. 328–340.

Gerard et al., "Influence on Stability in *Escherichia coli* of the Carboxy–Terminal Structure of Cloned Moloney Murine Leukemia Virus Reverse Transcriptase," DNA, vol. 5, No. 4 (Aug. 1986), pp. 271–279.

Telesnitsky et al., "RNase H domain mutations affect the interaction between Moloney murine leukemia virus reverse transcriptase and its primer–template," Proc. Natl. Acad. Sci. USA, vol. 90, (Feb. 1993), pp. 1276–1280.

Blain et al., "Nuclease Activities of Moloney Murine Leukemia Virus Reverse Transcriptase," The Journal of Biological Chemistry, vol. 268, No. 31, (Nov. 5, 1993), pp. 23585–23592.

B1 5,405,776

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1, 2, 3, 4, 5, 6, 7, 8, and 9 is confirmed.

* * * * *